(12) United States Patent
Schuler et al.

(10) Patent No.: US 12,097,455 B1
(45) Date of Patent: Sep. 24, 2024

(54) ULTRAVIOLET RETURN VENT AIR FILTER

(71) Applicants: Chris Schuler, Chapel Hill, TN (US); John Thomas Goodwin, Nashville, TN (US)

(72) Inventors: Chris Schuler, Chapel Hill, TN (US); John Thomas Goodwin, Nashville, TN (US)

(*) Notice: Subject to any disclaimer, the term of this patent is extended or adjusted under 35 U.S.C. 154(b) by 0 days.

(21) Appl. No.: 18/512,549

(22) Filed: Nov. 17, 2023

(51) Int. Cl.
  *B01D 46/00* (2022.01)
  *A61L 9/20* (2006.01)
  *B01D 46/42* (2006.01)

(52) U.S. Cl.
  CPC ............ *B01D 46/0028* (2013.01); *A61L 9/20* (2013.01); *B01D 46/4245* (2013.01); *A61L 2209/11* (2013.01); *A61L 2209/14* (2013.01); *A61L 2209/16* (2013.01); *B01D 2279/50* (2013.01)

(58) Field of Classification Search
  CPC ............ B01D 46/0028; B01D 46/0005; B01D 46/0086; B01D 46/0091; B01D 46/4245; B01D 46/442; B01D 46/448; A61L 9/20; A61L 2209/15; A61L 2209/14; A61L 2209/111
  USPC ........ 55/385.2, 484, 489, DIG. 31, DIG. 34; 96/397; 422/24, 121, 186.07
  See application file for complete search history.

(56) References Cited

U.S. PATENT DOCUMENTS

| | | | | |
|---|---|---|---|---|
| 4,792,345 A | * | 12/1988 | Abe | F24F 8/192 55/467 |
| 5,837,207 A | * | 11/1998 | Summers | A61L 9/20 250/504 R |
| 6,132,784 A | * | 10/2000 | Brandt | A23L 3/28 422/186.3 |
| 6,464,760 B1 | | 10/2002 | Sham et al. | |
| 6,500,387 B1 | * | 12/2002 | Bigelow | A61L 9/20 55/286 |
| 6,849,107 B1 | * | 2/2005 | Huffman | B01D 46/521 261/80 |
| 7,740,810 B2 | | 6/2010 | Hay et al. | |
| 8,691,144 B2 | | 4/2014 | Garfield et al. | |
| 9,039,966 B2 | * | 5/2015 | Anderson | A61L 2/084 422/4 |
| 9,518,487 B2 | * | 12/2016 | Coelho Ferreira | B03C 3/41 |

(Continued)

OTHER PUBLICATIONS

Amazon.com—Air Health Haven Plus HVAC Air Purifier, printed from the Internet at https://www.amazon.com/Health-Haven-Purifier-Carbon-Installation/dp/B0924X64B5/ref=sr_1_3?crid=17YBWOP52H6UJ&keywords=Air+Health+Haven+Plus+HVAC+Air+Purifier&qid=1696709812&sprefix=air+health+haven+plus+hvac+air+purifier%2Caps%2C85&sr=8-3 on Jul. 19, 2023, Apr. 21, 2021.

(Continued)

*Primary Examiner* — Minh Chau T Pham
(74) *Attorney, Agent, or Firm* — Trenner Law Firm, LLC; Mark Trenner

(57) ABSTRACT

An ultraviolet (UV) air filter device for an HVAC system is disclosed. An example UV air filter device may include a body having a support structure and a filtration media. The example UV air filter device may also include a plurality of ultraviolet (UV) lights provided in the filtration media itself and/or mounted to the support structure. The example UV air filter device may also include a power source to provide electrical energy to the plurality of UV lights. The example UV air filter device may also include a fan or fan device, fan prop or rotor blade to circulate air across the UV lights.

13 Claims, 11 Drawing Sheets

(56) References Cited

U.S. PATENT DOCUMENTS

| | | | | |
|---|---|---|---|---|
| 9,587,846 | B2* | 3/2017 | Dobbyn | B01D 46/46 |
| 9,937,453 | B2* | 4/2018 | Baek | F24F 8/108 |
| 10,092,672 | B2 | 10/2018 | Hingorani et al. | |
| 10,357,582 | B1* | 7/2019 | Barron | H01L 25/0753 |
| 10,363,325 | B2* | 7/2019 | Hawkins | F21S 8/026 |
| 10,413,626 | B1* | 9/2019 | Barron | A61L 2/084 |
| 10,946,321 | B1* | 3/2021 | Hamidzai | B01D 46/0028 |
| 2004/0146437 | A1* | 7/2004 | Arts | A61L 2/10 |
| | | | | 422/186.3 |
| 2007/0220851 | A1* | 9/2007 | Parker | F24F 8/22 |
| | | | | 55/484 |
| 2008/0266758 | A1* | 10/2008 | Hurt | F03D 9/11 |
| | | | | 361/625 |
| 2014/0238244 | A1* | 8/2014 | Chin | B01D 46/76 |
| | | | | 55/473 |
| 2018/0363624 | A1* | 12/2018 | Focanti | F03D 3/061 |

OTHER PUBLICATIONS

Amazon.com—D200 Dual Lamp Air Purifier Whole House Filter UV Light in Duct for HVAC Ac (Air Conditioning) Duct Germicidal, printed from the Internet at whttps://www.amazon.com/D200-PCO-photocatalytic-Conditioning-Germicidal/dp/B0754C889Z/ref=sr_1_1?crid=3G3UX2EAAXHML&keywords=D200+Dual+Lamp+Air+Purifier+Whole+House+Filter+UV+Light+in+Duct+for+HVAC+AC+%28Air+Conditioning%29+Duct+Germicidal&qid=1696709886&sprefix=d200+dual+lamp+air+purifier+whole+house+filter+uv+light+in+duct+for+hvac+ac+air+conditioning+duct+germicidal%2Caps, Aug. 25, 2017.

* cited by examiner

ULTRAVIOLET RETURN VENT AIR FILTER

BACKGROUND

Air filtration is important for helping to reduce allergies and odors caused by airborne particles. There are a variety of different types of air filters available for residential and commercial heating, ventilation and air conditioning (HVAC) systems. Different filters types, sizes, and filtration media may be used, depending what the user wants to remove from the air. These filters are commonly installed on the return vent in the HVAC system, but may also be installed closer to the HVAC blower unit. These filters function well to remove common household particles, such as dust, dander, and pollen. Most filters do little if anything to help reduce airborne viruses, mold spores, and other contaminants that can cause illness.

DETAILED DESCRIPTION

Figure 1:
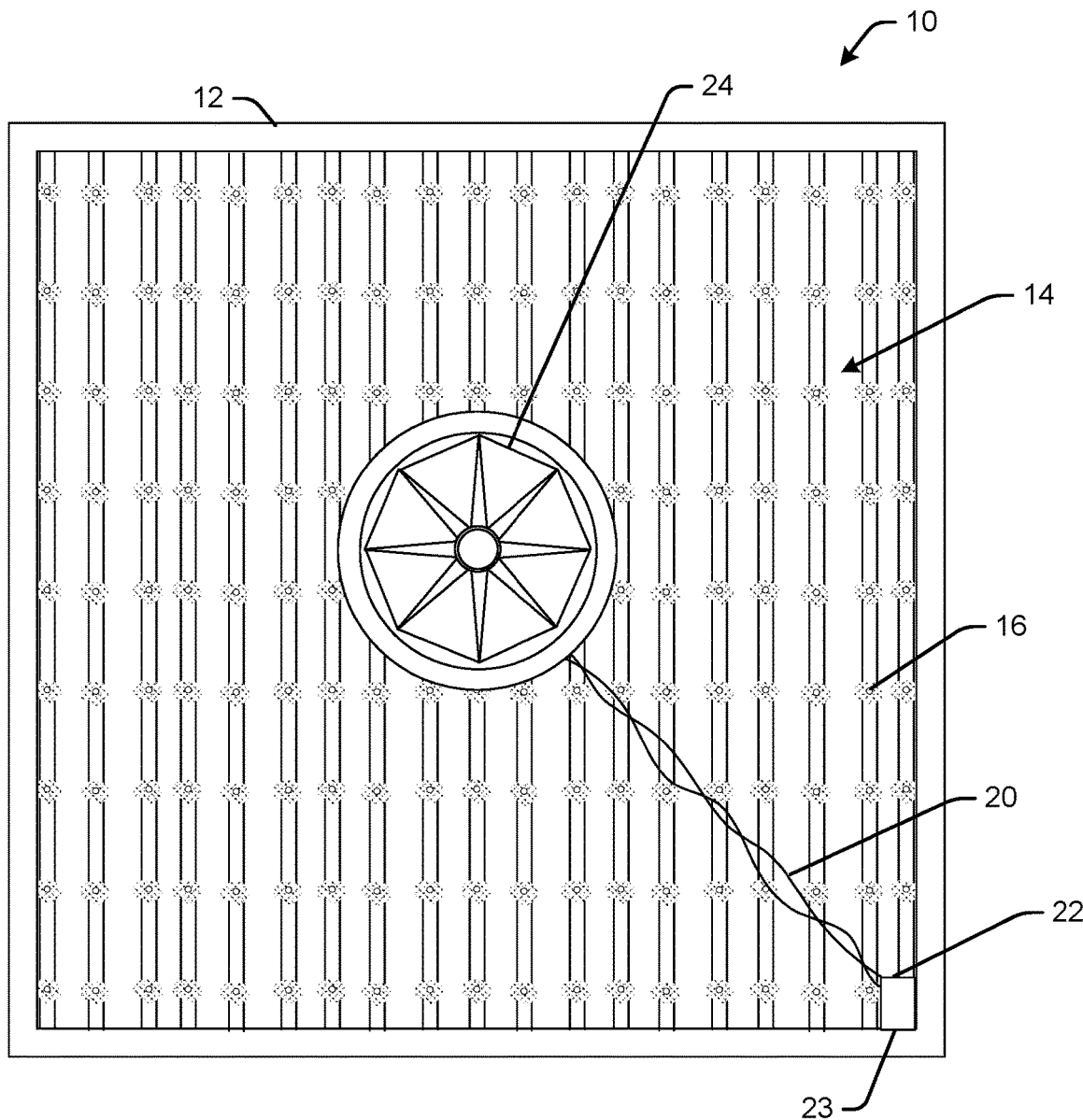
FIG. 1 is a front view of an example ultraviolet (UV) air filter device with fan housing, positive and negative wires, circuit box and UV LED lights, fan device, fan prop or rotor blade or fan device.

An ultraviolet (UV) air filter device is disclosed which may be provided for a return vent for an HVAC system. The UV air filter device may be implemented to help purify air by removing bacteria, particulates, mold spores, viruses and other contaminants with UVA, UVB, and UVC light. Having UV light may also help the body produce more vitamin D.

An example ultraviolet (UV) air filter device for an HVAC system includes a body having a support structure for a square or rectangular filtration media. A plurality of ultraviolet (UV) lights is provided in the filtration media itself and/or mounted to the support structure. An indoor wind turbine microgenerator is made operational by a flow of indoor air supply generated by the HVAC system. Control circuitry and a battery is connected between the indoor wind turbine microgenerator and the plurality of UV lights to solely provide direct current (DC) electrical power generated by the indoor wind turbine microgenerator through the battery to the plurality of UV lights. A control box includes a circuit board with the control circuitry. The UV lights output at least one of UVA light, UVB light, UVC light, and infrared (IR) light to provide antimicrobial air filtration.

An example UV air filter device includes micro UV light emitting diodes (LEDs) tuned or otherwise configured to generate UVA, UVB, UVC and/or a combination of the UV light spectrum. The UV lights may be integrated into or otherwise provided in a structure suitable for residential, commercial, and/or industrial HVAC systems in a home or building. UV and/or other LED lights may also be provided for a decorative effect.

An example UV air filter device is powered by any of a variety of different power sources, such as but not limited to, cordless power sources such as low voltage battery or micro-wind turbine generators, and a wireless battery source so that it charges wirelessly. The example UV air filter device may also be powered by corded power sources, such as Universal Serial Bus (USB) power. or traditional 120 volt household plugs and an external fan generator.

An example UV air filter device may include disposable and/or reusable filters. If the filter is disposable, the lighting system may be provided as part of a support structure from which the filter media is removable, so that the filter can be changed without having to replace the lighting system. If the filter is reusable, the lighting system may be integrated into the filter itself. For example, micro UV lights may be attached to the surface of the filter, woven in and out of the filter and/or lined in between two pieces of filter material. If the UV air filter model is disposable the whole unit may be thrown away and replaced.

In an example, the UV air filter device provides a relatively inexpensive, simple, and easy solution to purifying the air people breathe within their home and work areas. It can help to reduce bacteria and viruses including Covid 19 and other forms of airborne viruses (e.g., Severe Acute Respiratory Syndrome or SARS). It also may also help to sterilize many other contaminants that pass through the air filters that might not otherwise be caught by the filter media and thus be recirculated back into the air.

Before continuing, it is noted that as used herein, the terms "includes" and "including" mean, but is not limited to, "includes" or "including" and "includes at least" or "including at least." The term "based on" means "based on" and "based at least in part on."

It is also noted that the examples shown and described herein are provided for purposes of illustration, and are not intended to be limiting. Other devices and/or structural configurations may be utilized to carry out the operations described herein.

The operations shown and described herein are provided to illustrate example implementations. It is noted that the operations are not limited to the ordering shown. Still other operations may also be implemented.

FIG. 1 is a front view of an example ultraviolet (UV) air filter device 10 which may be provided for a return vent for an HVAC system. The example air filter device 10 may include a support structure or body 12 for a filtration media 14 and ultraviolet (UV) light emitting diode (LED) lighting 16. The UV air filter device 10 may also include positive and negative wires 20 for providing direct current (DC) power from a power source, a circuit box 22 (e.g., housing a circuit board and/or battery or other power source 23, and a fan device 24 including one or more fan prop or rotor blade.

Figure 2:
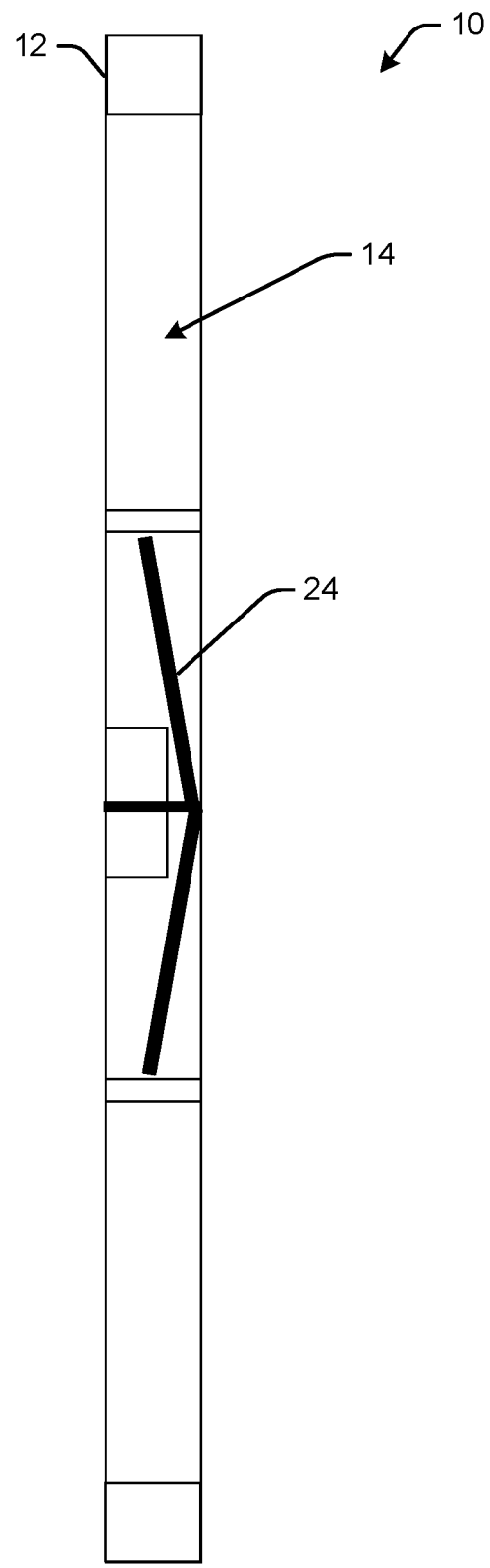
FIG. 2 is a side cross-sectional view of the example UV air filter device corresponding to FIG. 1.
Figure 3:
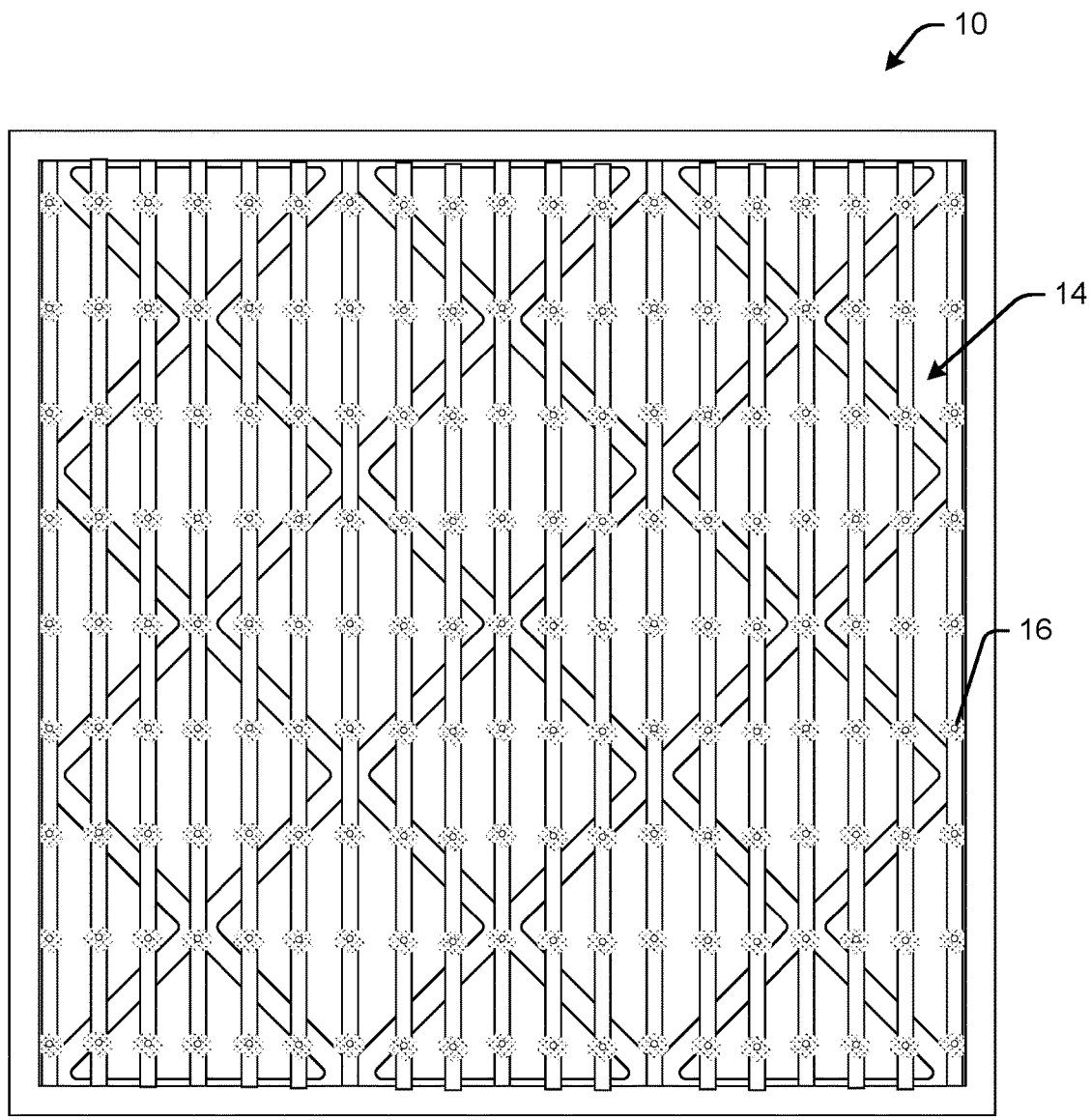
FIG. 3 is a rear view of the example UV air filter device corresponding to FIG. 1 with the filter media removed.
Figure 4:
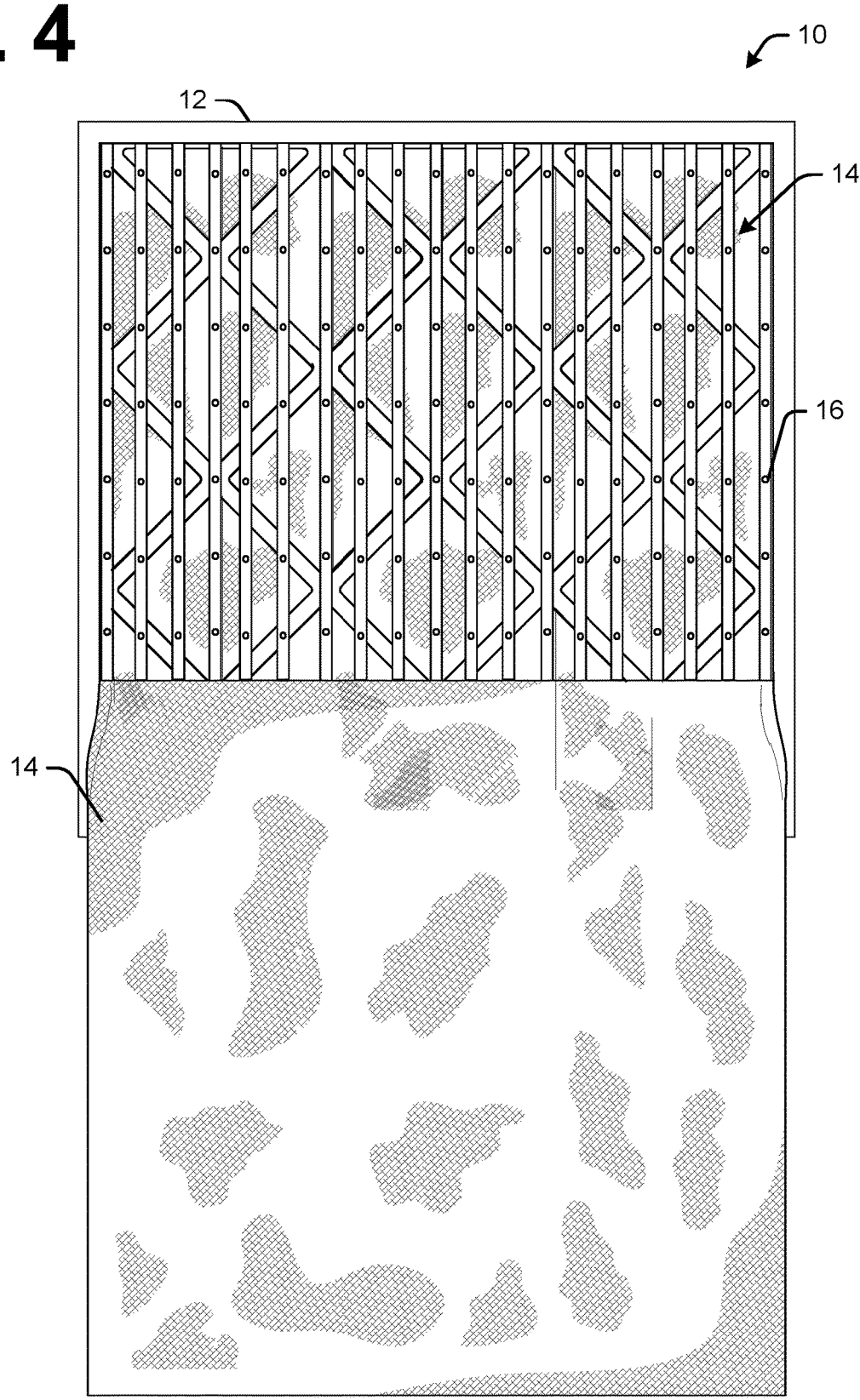
FIG. 4 is a rear view of the example UV air filter device corresponding to FIG. 1 showing the filter media partially removed.
Figure 5:
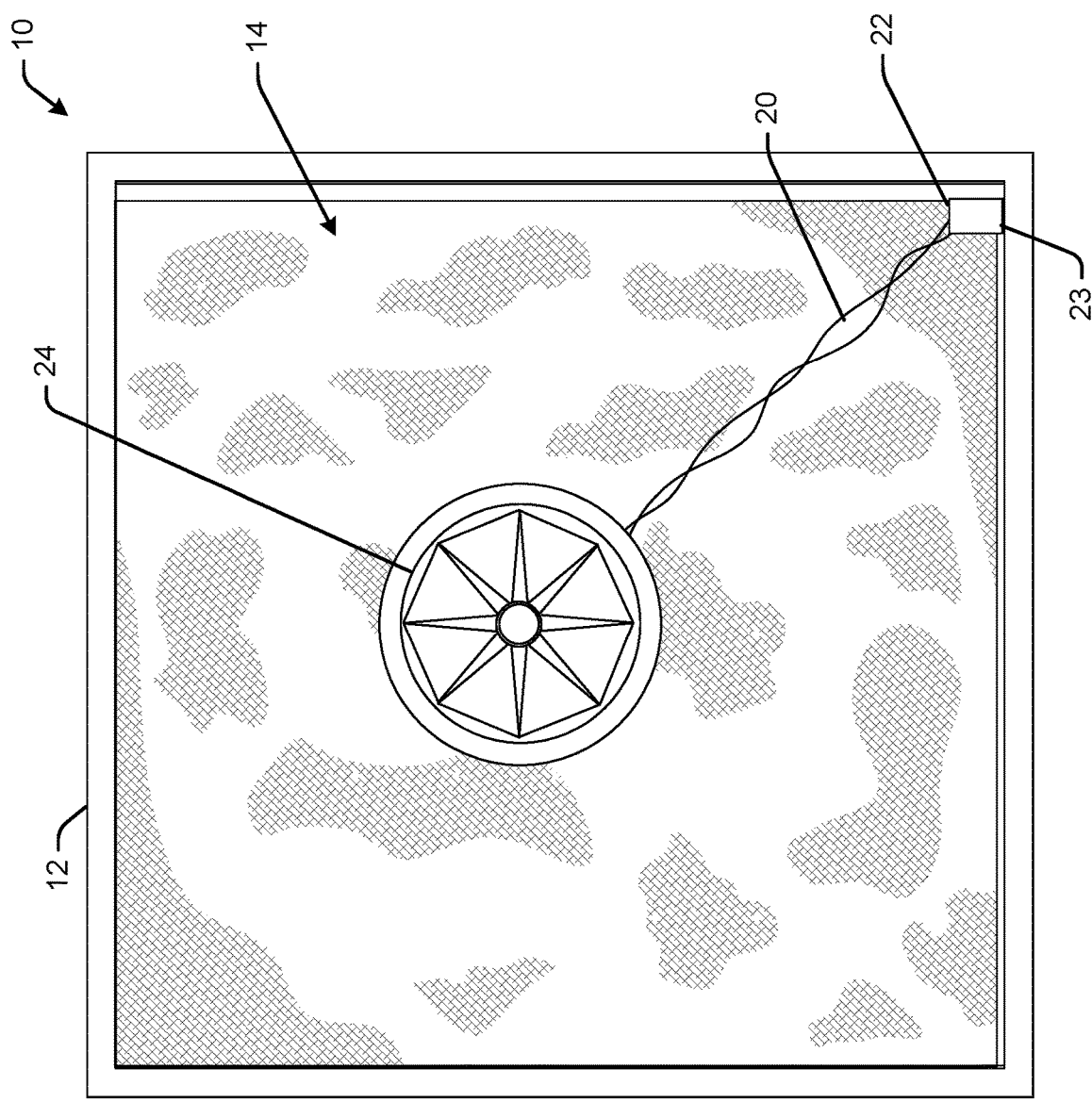
FIG. 5 is a rear view of the example UV air filter device corresponding to FIG. 1 showing an example of UV LED light patterns.

FIG. 2 is a side cross-sectional view of the example UV air filter device 10 corresponding to FIG. 1. FIG. 3 is a rear view of the example UV air filter device 10 corresponding to FIG. 1 with the filter media 14 removed. FIG. 4 is a rear view of the example UV air filter device 10 corresponding to FIG. 1 showing the filter media 14 partially removed. FIG. 5 is a rear view of the example UV air filter device 10 corresponding to FIG. 1 showing an example of UV LED light patterns.

An example of the UV air filter device 10 for an HVAC system includes a body 12 having a support structure and a filtration media 14. A plurality of ultraviolet (UV) lights 16 are provided in the filtration media itself and/or mounted to the support structure. A power source 23 (e.g., disposable or rechargeable batteries) and associated control circuitry 22 provide electrical energy to the UV lights 16. The UV lights are configured to output at least one of UVA light, UVB light, UVC light, and infrared (IR) light to provide antimicrobial air filtration.

The example UV air filter device 10 may also include one or more fan or other fan device, fan prop or rotor blade assembly 24 mounted to the body 12 (e.g., on the support structure). The fan blades can be made out of any type of material and be in any shape and size. Bladeless fans may also be provided. During operation, the fan or fan device, fan prop or rotor blade assembly 24 circulates air across the UV lights 16 to enhance the air sterilization.

In an example, the fan or fan device, fan prop or rotor blade assembly 24 is mounted flush with the support structure 12 and/or the filtration media 16. In an example, the fan or fan device, fan prop or rotor blade assembly 24 is mounted outside of the support structure 12. In an example, a separate power source may be provided for the supplemental fan device 24, fan prop or rotor blade and a separate power source may be provided for the UV lights 14.

In an example, the filtration media 14 is disposable and the body 12 and the plurality of UV lights 16 are reusable by replacing the filtration media 14.

In an example, the support structure 12 includes an outer frame and a first plurality of cross members crossing in a first direction, and a second plurality of cross members crossing in a second direction. The plurality of UV lights 16 span a space formed between the first plurality of cross members and the second plurality of cross members. For example, the plurality of UV lights 16 may span from a first edge of the support structure to a second edge of the support structure. The plurality of UV lights 14 may span between opposite edges of the support structure 12.

In an example, the UV lights 16 are wireless, and the power source 23 for the UV lights is wirelessly recharged.

Figure 6:
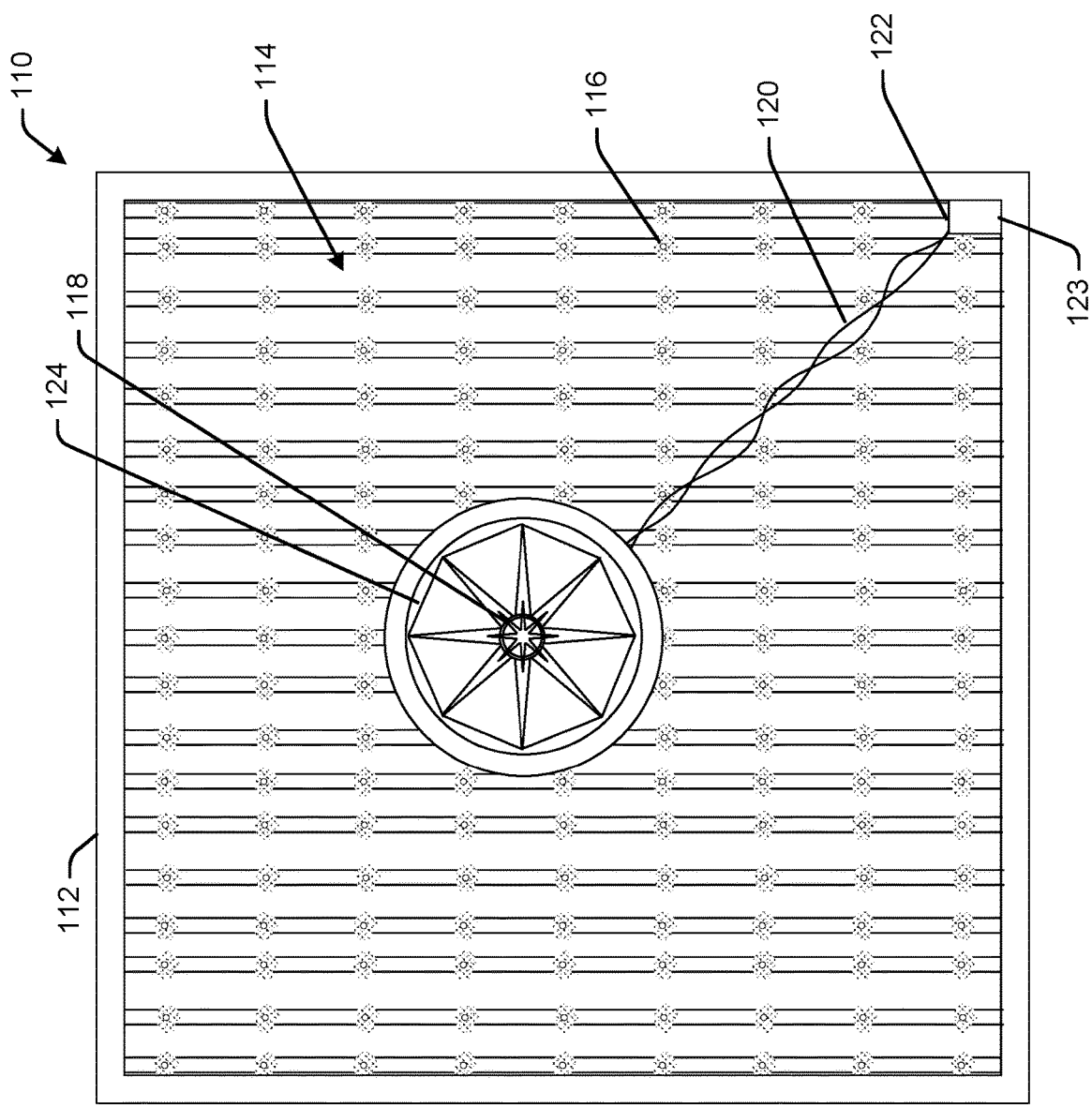
FIG. 6 is a front view of another example ultraviolet (UV) air filter device with a micro-generator.

FIG. 6 is a front view of another example ultraviolet (UV) air filter device 110 with a supplemental or secondary generator, such as a micro-generator 118. It is noted that 100-series reference numbers are used in FIG. 6 to refer to like components already described above.

In an example, the power source includes an electrical microgenerator 118 (e.g., having a wind turbine) to provide direct and/or regenerative electricity. Direct electricity, as that term is used herein, is provided directly to the UV lights 116. Regenerative electricity, as that term is used herein, refers to electricity that is provided to the battery, which in turn powers the UV lights 116.

In an example, the wind turbine of the electrical microgenerator 118 rotates in response to airflow produced by the HVAC system. The airflow produced by the HVAC system may be either airflow blown out from the vent system (where the UV air filter device 110 is installed on a vent register), or airflow received through the air return (where the UV air filter device 110 is installed on a return vent). The electrical microgenerator 118 may be configured to convert the rotational energy of the wind turbine into the electricity for one or more components of the UV air filter device 110 and/or other devices (e.g., decorative LED lighting on or separate from the UV air filter device 110).

In an example, the microgenerator 118 may include multiple fans and/or power sources positioned in any suitable location(s) in the UV air filter device 110 and/or at least partly internal thereto.

Figure 7:
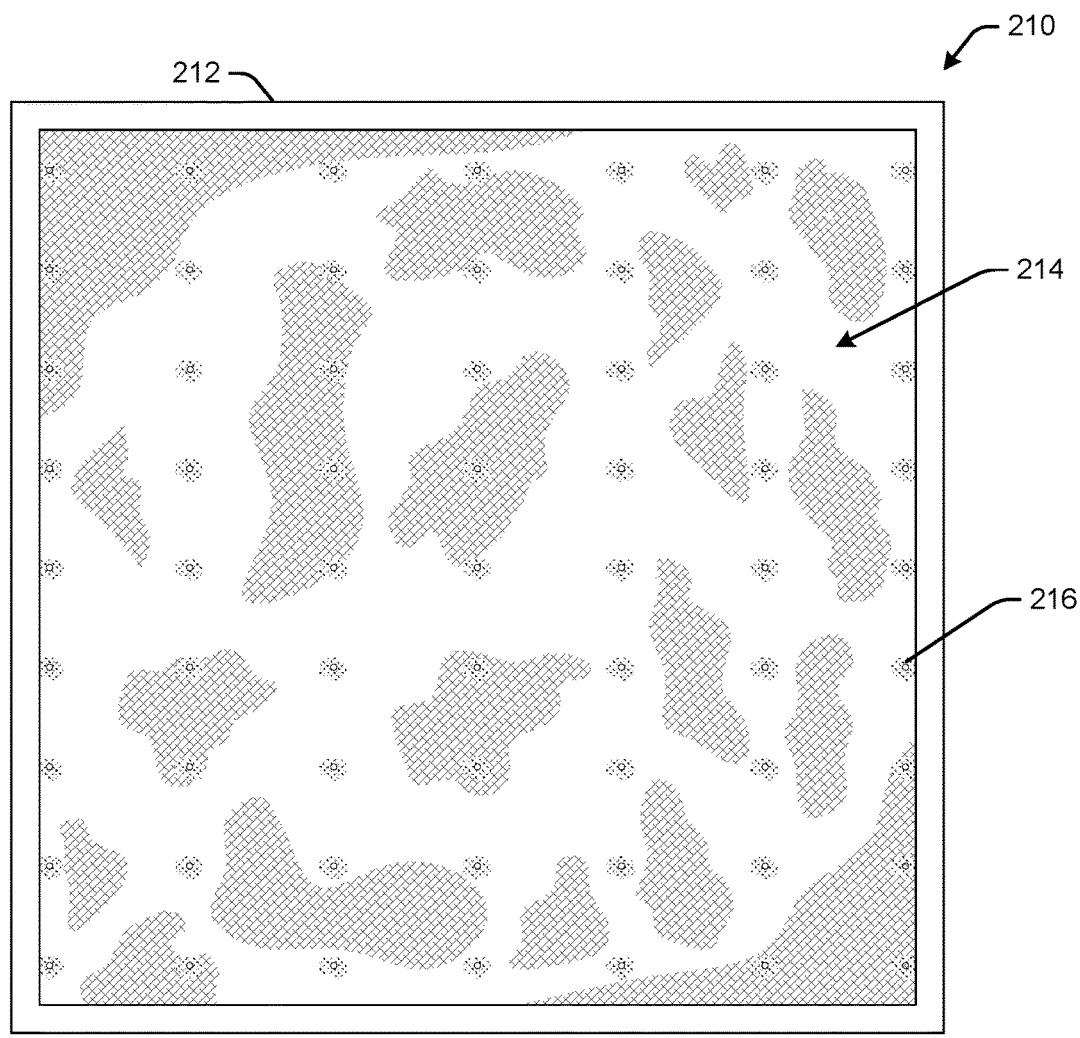
FIG. 7 is a front view of another example ultraviolet (UV) air filter device with light emitting diode (LED) lighting embedded in the filter material.

FIG. 7 is a front view of another example ultraviolet (UV) air filter device 210 with the light emitting diode (LED) lighting 216 embedded in the filter material. It is noted that 200-series reference numbers are used in FIG. 7 to refer to like components already described above.

As described above with reference to FIG. 1, the UV air filter device 10 is shown including the plurality of UV lights 16 provided only on one side of the filtration media. In the example shown in FIG. 7, the UV air filter device 210 includes the plurality of UV lights 216 are embedded in the filtration media 214 and/or between layers of the filtration media 214.

Figure 8:
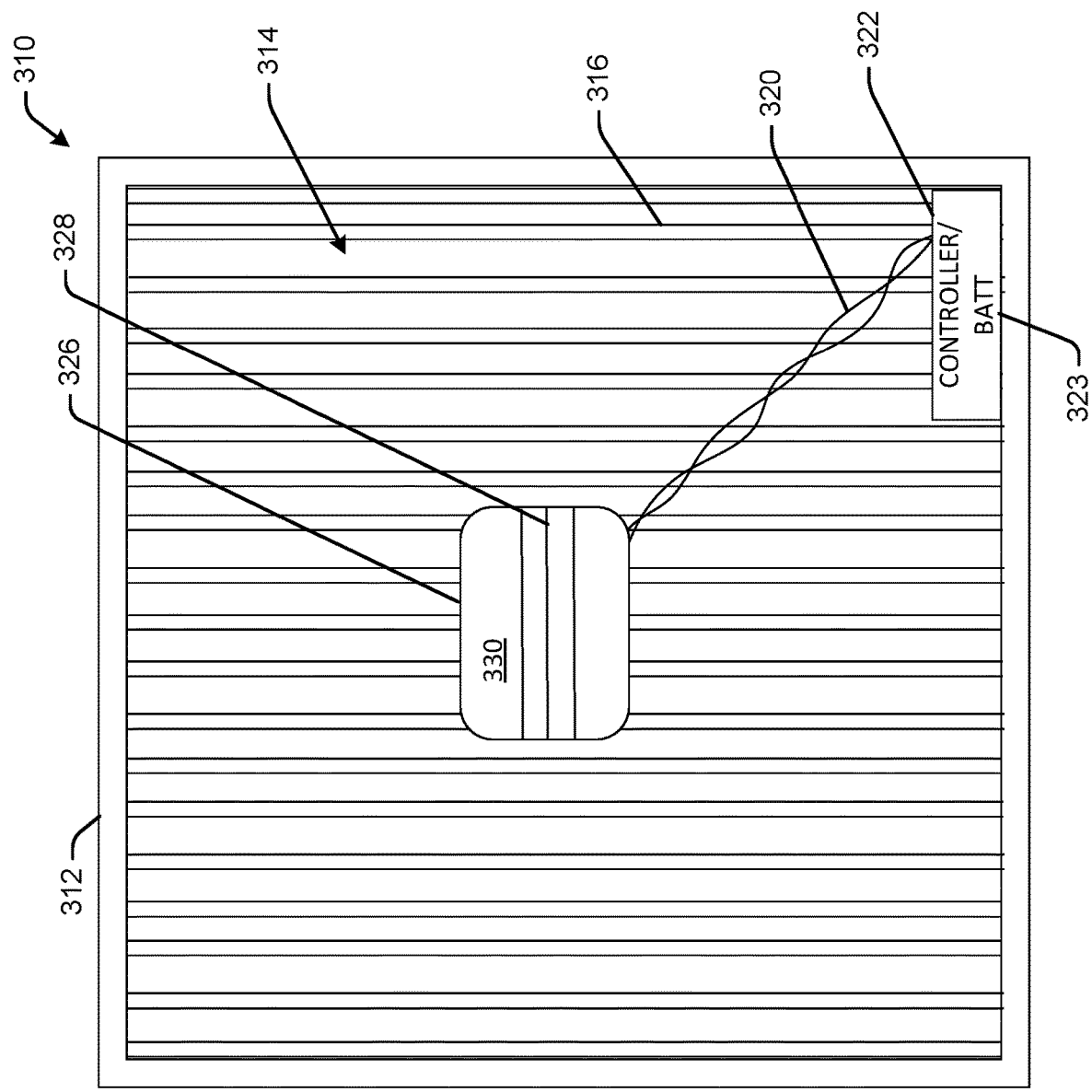
FIG. 8 is a front view of another example ultraviolet (UV) air filter device with an air-operated switch that completes the circuit to the battery pack.
Figure 9:
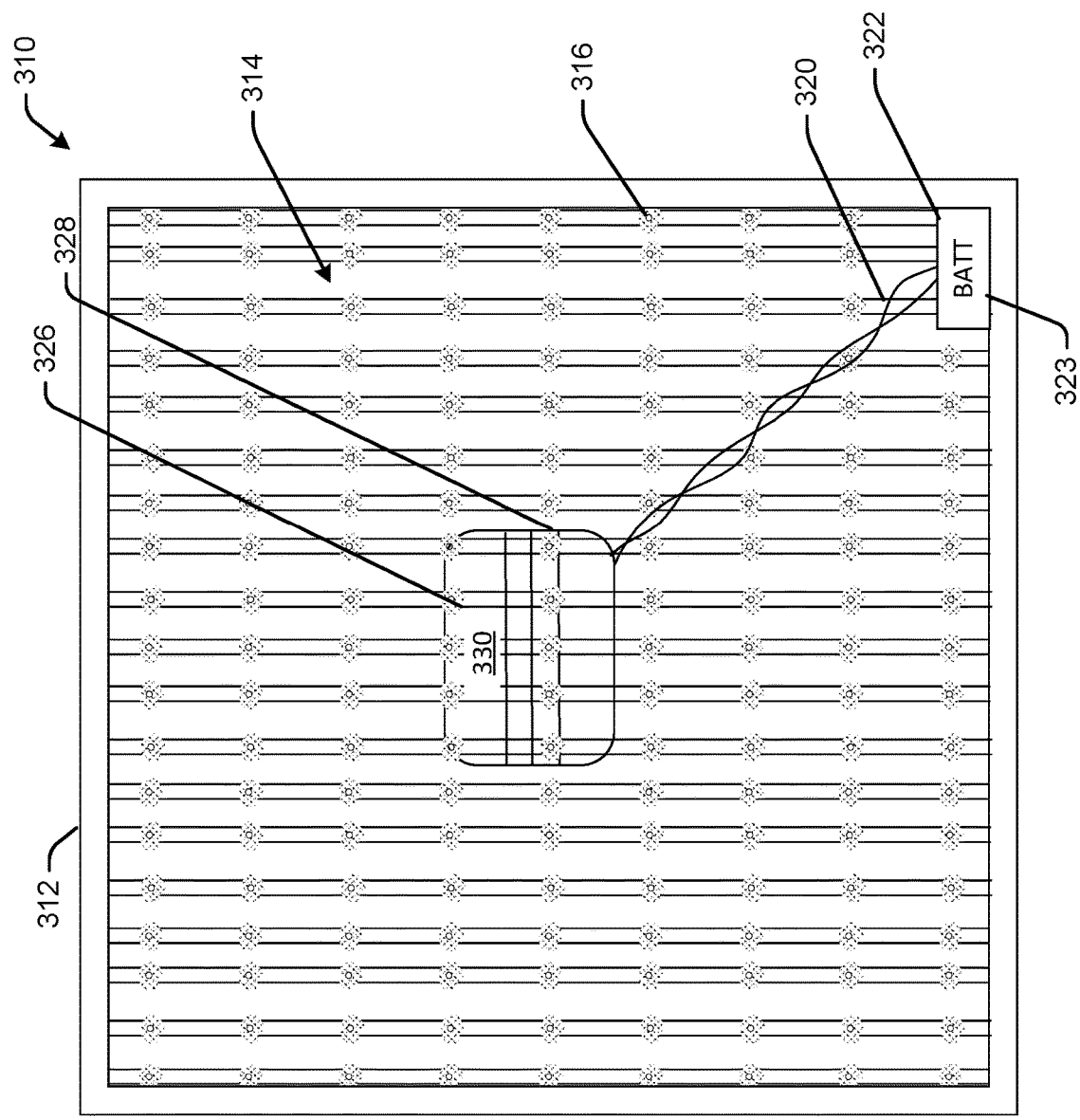
FIG. 9 is a rear view of the example ultraviolet (UV) air filter device corresponding to FIG. 8.

FIG. 8 is a front view of another example ultraviolet (UV) air filter device 310 with an airflow operated switch 326 that completes the circuit to the battery 223. FIG. 9 is a rear view of the example ultraviolet (UV) air filter device corresponding to FIG. 8. It is noted that 300-series reference numbers are used in FIGS. 8 and 9 to refer to like components already described above.

The UV air filter device 310 may include an airflow actuated switch 326 to automatically provide electrical power from the power source 323 to the UV lights in response to HVAC airflow through the filtration media. As noted above, the airflow produced by the HVAC system may be either airflow blown out from the vent system (where the UV air filter device 310 is installed on a vent register), or airflow received through the air return (where the UV air filter device 310 is installed on a return vent).

The airflow actuated switch 326 may include a switching element 328 configured to switch to an open or ON position (e.g., when airflow opens the flaps or switching element 328). The switching element 328 of the airflow actuated switch 326 is also configured to switch to a closed or OFF position (e.g., when airflow is insufficient to open the flaps or switching element 328).

More specifically, an example airflow actuated switch 326 includes the switching element 328, at least one opening formed therethrough, and a cover (or door or flap) 330 biased in a closed position. The cover 330 moves to at least a partly or even fully open position in response to sufficient airflow through the filtration media 314 such that the airflow overcomes the bias and opens so that the position of the cover 330 activates the switching element 328. When airflow slows such that the bias controls, the cover 330 closes and deactivates the switching element 328 (cutting or reducing electrical power). The bias may be provided by a spring or other resilient element.

In another example, the switching element need not be air activated. For example, the switching element may be manually activated (switched) and/or may be activated automatically by a sensor or a signal from the thermostat.

In an example, activating the switching element 328 actuates the power source to provide electrical power to the UV lights in response to operation of the HVAC system. Deactivating the switching element 328 turns off the electrical power to the UV lights from the power source and/or other electrically powered elements (e.g., decorative LED lighting) that are part of or at least electrically connected with the UV air filter device.

Figure 10:
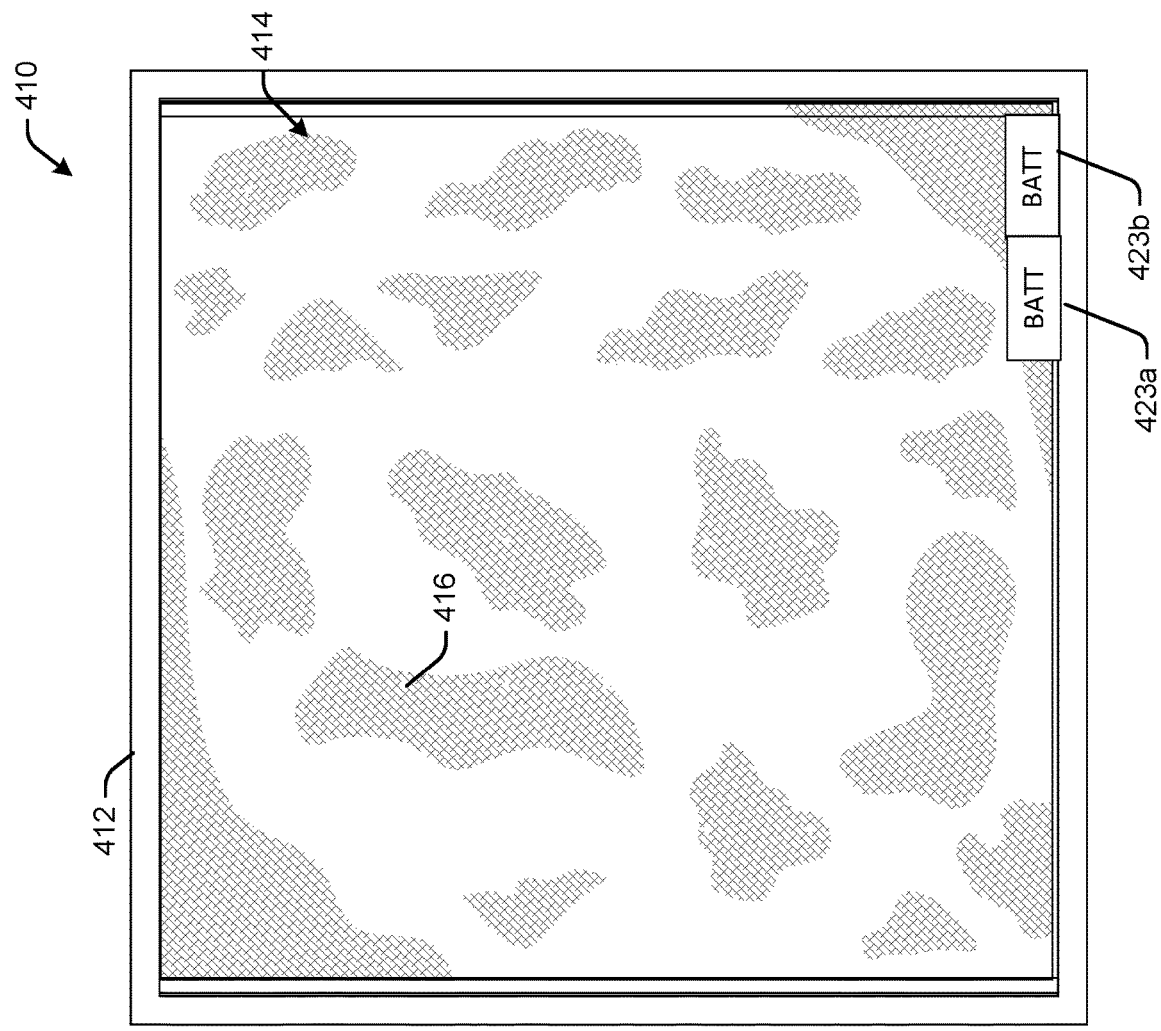
FIG. 10 is a front view of another example ultraviolet (UV) air filter device with a battery for the LED lighting.

FIG. 10 is a front view of another example ultraviolet (UV) air filter device 410 with a battery for the LED lighting. It is noted that 400-series reference numbers are used in FIG. 10 to refer to like components already described above.

An example UV air filter device 410 may also include one or more power source 423a, 423b. This may be the same power source that powers both the UV lights and the fan, or the power source 423a, 423b for the fan or fan device, fan prop or rotor blade assembly may be a separate power source from the power source that powers the UV lights.

In an example, a separate or "first" power source(s) 423a provides electrical energy to the plurality of UV lights, and a separate or "second" second power source 423b provides electrical energy to the fan or fan device, fan prop or rotor blade assembly.

In an example, the power source 423a, 423b is wirelessly recharged.

In an example, the UV lights are wireless and operated by individual batteries embedded in the UV lights.

Figure 11:
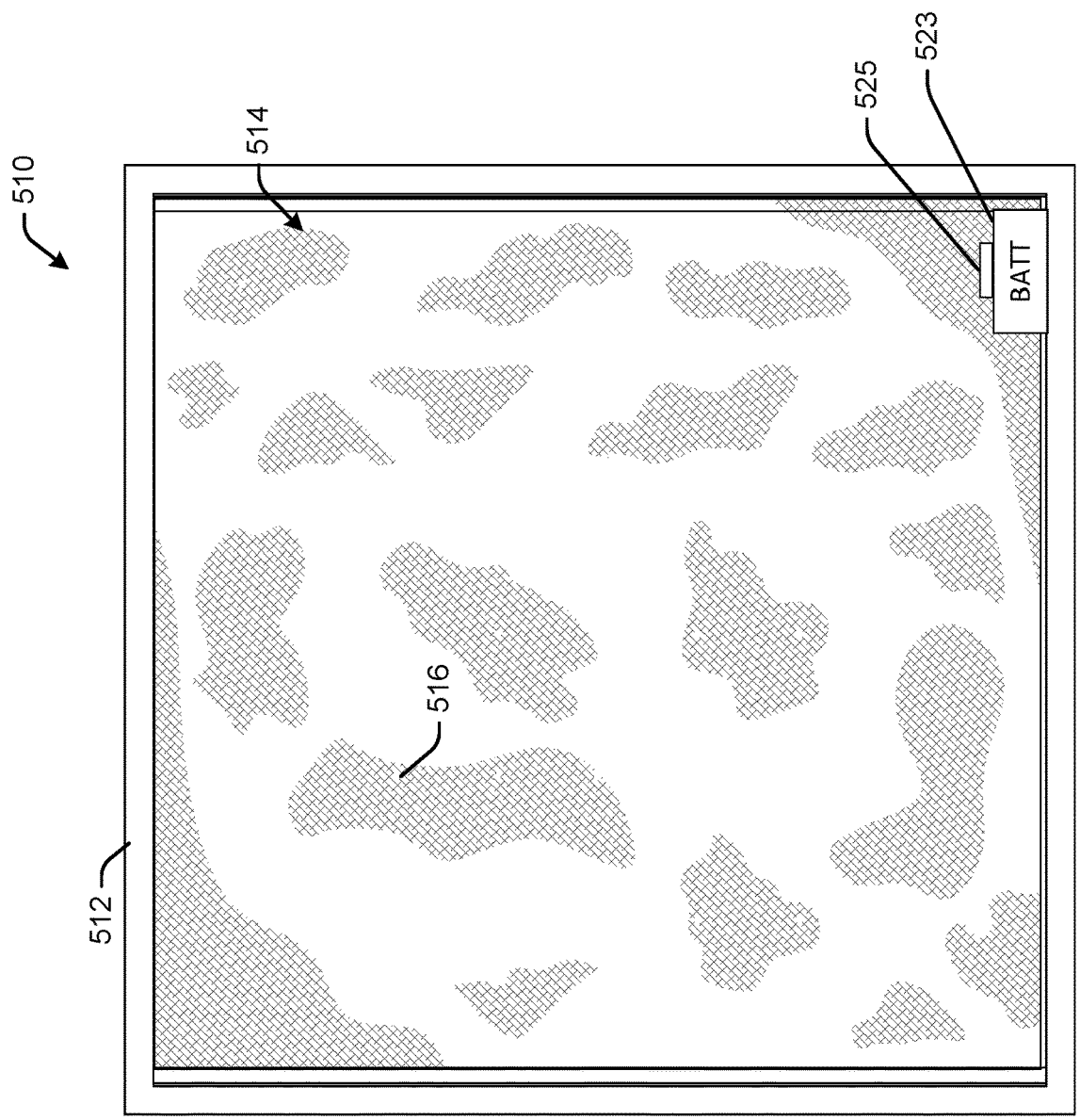
FIG. 11 is a front view of another example ultraviolet (UV) air filter device with a battery and switch device for the LED lighting.

FIG. 11 is a front view of another example ultraviolet (UV) air filter device 510 with a battery 523 and switch device 525. It is noted that 500-series reference numbers are used in FIG. 10 to refer to like components already described above. The switch device 525 may be manually operated, e.g., to activate the UV lighting.

It is noted that the examples shown and described are provided for purposes of illustration and are not intended to be limiting. Still other examples are also contemplated.

The invention claimed is:

1. An ultraviolet (UV) air filter device for an HVAC system, comprising:
    a body having a support structure for a square or rectangular filtration media;
    a plurality of ultraviolet (UV) lights provided in the filtration media itself and/or mounted to the support structure;
    an indoor wind turbine microgenerator made operational by a flow of indoor air supply generated by the HVAC system;
    control circuitry connecting the indoor wind turbine microgenerator and the plurality of UV lights to solely provide direct current (DC) electrical power generated from the indoor wind turbine microgenerator to the plurality of UV lights; and
    a control box including a circuit board with the control circuitry;
    wherein the UV lights output at least one of UVA light, UVB light, UVC light, and infrared (IR) light to provide antimicrobial air filtration.

2. The device of claim 1, further comprising an airflow actuated switch to automatically provide electrical power from a power source to the UV lights in response to HVAC airflow through the filtration media.

3. The device of claim 2, wherein the airflow actuated switch further comprises:
    a switching element;
    at least one opening formed therethrough; and
    a cover biased in a closed position, the cover moving to at least a partly open position in response to sufficient airflow through the filtration media such that the airflow overcomes the bias, the position of the cover activating and deactivating the switching element;
    wherein activating the switching element actuates the power source to provide electrical power to the UV lights in response to operation of the HVAC system and deactivating the switching element turns off the electrical power to the UV lights from the power source.

4. The device of claim 1, wherein the filtration media is disposable and the body and the plurality of UV lights are reusable by replacing the filtration media.

5. The device of claim 1, wherein the support structure includes an outer frame and a first plurality of cross members crossing in a first direction, and a second plurality of cross members crossing in a second direction, wherein the plurality of UV lights span a space formed between the first plurality of cross members and the second plurality of cross members.

6. The device of claim 1, wherein the plurality of UV lights span from a first edge of the support structure to a second edge of the support structure.

7. The device of claim 1, wherein the plurality of UV lights span between opposite edges of the support structure.

8. The device of claim 1, wherein the plurality of UV lights are provided only on one side of the filtration media.

9. The device of claim 1, wherein the plurality of UV lights are embedded between first and second layers of the filtration media.

10. The device of claim 1, wherein the UV lights are wireless.

11. An ultraviolet (UV) air filter device, comprising:
    a body having a support structure for a square or rectangular filtration media;
    a plurality of ultraviolet (UV) lights provided in the filtration media itself and/or mounted to the support structure, the UV lights spanning from a first side of the filtration media to a second side of the filtration media;
    an indoor wind turbine microgenerator made operational by a flow of indoor air supply generated by the HVAC system; and
    a control circuit and a battery connected between the indoor wind turbine microgenerator and the plurality of UV lights to solely provide direct current (DC) electrical power generated by the indoor wind turbine microgenerator through the battery to the plurality of UV lights.

12. An ultraviolet (UV) air filter device, comprising:
    a body having a support structure for a square or rectangular filtration media;
    a plurality of ultraviolet (UV) lights mounted in and/or adjacent to the filtration media, the UV lights outputting at least one of UVA light, UVB light, UVC light, and infrared (IR) light;
    an onboard battery supplying electrical energy solely to the plurality of UV lights;
    a control circuit and a battery connected solely between the indoor wind turbine microgenerator and the plurality of UV lights to solely provide direct current (DC) electrical power generated by the indoor wind turbine microgenerator through the onboard battery to the plurality of UV lights; and
    a control box including a circuit board with the control circuit connecting the plurality of the UV lights and the battery.

13. The device of claim 12, wherein the indoor wind turbine micro-generator is electrically connected to the onboard battery to recharge the onboard battery.

* * * * *